United States Patent [19]

Yonemoto et al.

[11] Patent Number: 5,112,989
[45] Date of Patent: May 12, 1992

[54] PROCESS FOR PRODUCING UNSATURATED MONO AND DICARBOXYLIC ACID IMIDE COMPOUND

[75] Inventors: Tatsuo Yonemoto, Hyogo; Eiichiro Saito; Masahiro Matsumura, both of Osaka, all of Japan

[73] Assignee: Matsushita Electric Works Ltd., Osaka, Japan

[21] Appl. No.: 325,807

[22] Filed: Mar. 20, 1989

[51] Int. Cl.$^5$ .............. C07D 403/06; C07D 207/40; C07D 207/448; C07D 207/452

[52] U.S. Cl. .................... 548/548; 548/518; 548/520; 548/521; 548/545; 548/454; 548/455; 548/473; 548/474

[58] Field of Search .............. 548/548, 518, 520, 521, 548/545, 474

[56] References Cited

FOREIGN PATENT DOCUMENTS 0257831 3/1988 European Pat. Off. .

OTHER PUBLICATIONS

Chemical Abstracts, vol. 110, 1989, p. 674, Abstract No. 57503k, Columbus, Ohio, U.S.; and JP-A-63 227 568 (Matsushita Electric Works, Ltd.) Sep. 21, 1988.
Tetrahedron Letters, vol. 39, No. 9, 1983, pp. 1475-1485, Pergamon Press Ltd., GB.
Chemical Abstracts, vol. 92, 1980, p. 642, Abstract No. 110809c, Columbus, Ohio, U.S.; Ind. J. Chem., Sect. B 1979, 18b(3), 245-7.

*Primary Examiner*—David B. Springer
*Attorney, Agent, or Firm*—Sughrue, Mion, Zinn, Macpeak & Seas

[57] ABSTRACT

A process for producing an unsaturated dicarboxylic acid imide compound of formula (I):

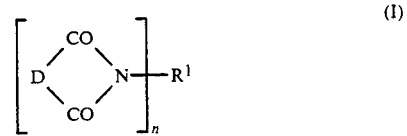

wherein D represents a divalent organic group having at least one carbon/carbon double bond; $R^1$ represents an n-valent organic group having at least one carbon atom; and n is an integer of 1 or above, which comprises reacting an unsaturated amide acid compound of formula (II):

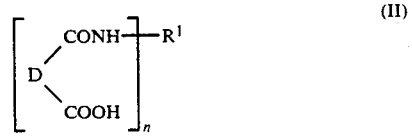

wherein D, $R^1$, and n are as defined above, with an orthoester of formula (III):

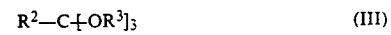

wherein $R^2$ and $R^3$, which may be the same or different, each represents a monovalent organic group having at least one carbon atom, to form an unsaturated dicarboxylic acid amide acid ester compound of formula (IV):

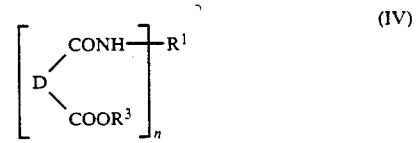

wherein D, $R^1$, $R^3$, and n are as defined above, and then imidating the compound of formula (IV).

12 Claims, 1 Drawing Sheet

PROCESS FOR PRODUCING UNSATURATED MONO AND DICARBOXYLIC ACID IMIDE COMPOUND

FIELD OF THE INVENTION

This invention relates to a novel process for producing an unsaturated dicarboxylic acid imide compound which can be used in, for example, the preparation of an addition type imide resin.

BACKGROUND OF THE INVENTION

One of known processes for producing an unsaturated dicarboxylic acid imide compound which is used in, for example, the preparation of an addition type imide resin comprises cyclizing an unsaturated amide acid compound. The cyclization may be conducted by, for example, a heat cyclization process described in JP-A-57-159764 (the term "JP-A" as used herein means a "published unexamined patent application") or a chemical cyclization process described in JP-A-53-23396.

The heat cyclization process literally comprises undergoing cyclization by heating to give approximately 93% by weight of a highly pure unsaturated dicarboxylic acid imide compound. However, this process requires a very long reaction period of time such as about 72 hours at the longest. Further, the cyclization is conducted through dehydration in a high energy state, which sometimes results in self-polymerization of part of the formed unsaturated dicarboxylic acid imide compound to thereby give a polymer. Consequently, the addition type imide resin prepared from this unsaturated dicarboxylic acid imide compound is somewhat disadvantageous in, for example, moldability.

The chemical cyclization process comprises undergoing cyclization by using a dehydrating agent such as acetic anhydride. Since this process can be completed at a low temperature within a short period of time, the obtained unsaturated dicarboxylic acid imide compound contains a small amount of polymer components. However, this process has some disadvantages such that the purity of the obtained unsaturated dicarboxylic acid imide compound is limited to approximately 90% at the highest.

SUMMARY OF THE INVENTION

Under these circumstances, the present invention has been made. That is, an object of the present invention is to provide a process for producing a highly pure unsaturated dicarboxylic acid imide compound within a short period of time at a low energy.

In order to achieve the above object, the present invention relates to a process for producing an unsaturated dicarboxylic acid imide compound of formula (I):

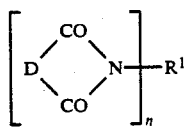
(I)

wherein D represents a divalent organic group having at least one carbon/carbon double bond; $R^1$ represents an n-valent organic group having at least one carbon atom; and n is an integer of 1 or above, which comprises reacting an unsaturated amide acid compound of formula (II):

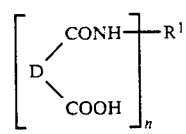
(II)

wherein D, $R^1$, and n are as defined above, with an orthoester of formula (III):

(III)

wherein $R^2$ and $R^3$, which may be the same or different, each represents a monovalent organic group having at least one carbon atom, to form an unsaturated dicarboxylic acid amide acid ester compound of formula (IV):

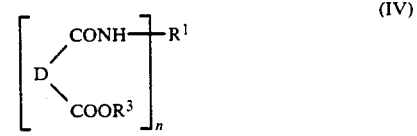
(IV)

wherein D, $R^1$, $R^3$, and n are as defined above, and then imidating the compound of formula (IV).

DETAILED DESCRIPTION OF THE INVENTION

Figure 1:
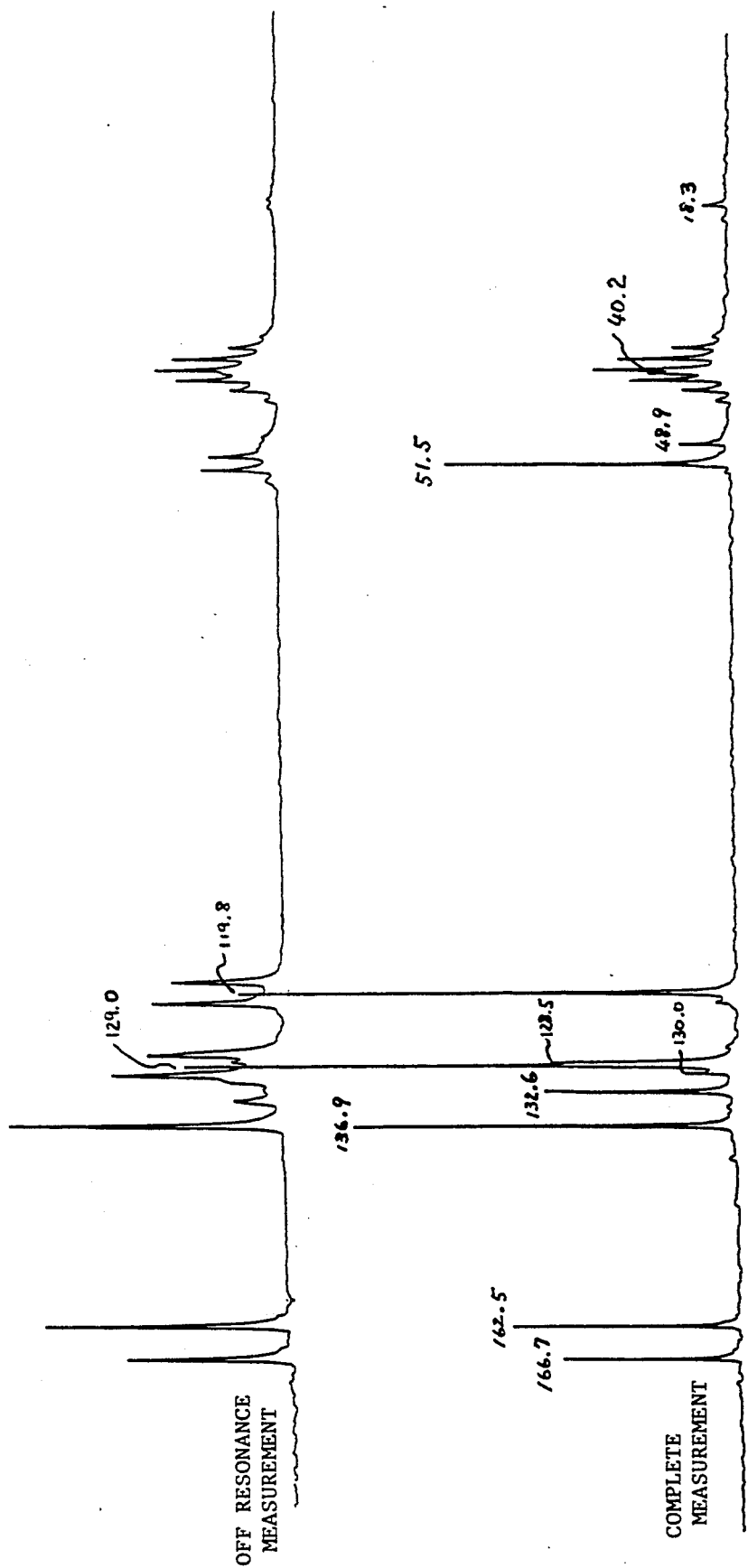
FIG. 1 is an NMR chart of the unsaturated dicarboxylic acid amide acid methyl ester obtained in Example 1.

The unsaturated amide acid compound of formula (II) which is used in the present invention can be obtained by any convenient method without particular restrictions. For example, it can be obtained by reacting an unsaturated dicarboxylic anhydride of the following formula:

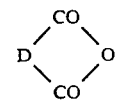

with an amine or polyamine represented by the following formula:

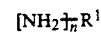

preferably in the presence of an organic solvent which is inert in the reaction system or in a non-solvent system.

In the foregoing formulae, specific examples of D include a group of the following formula:

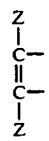

wherein Z represents hydrogen, an alkyl group, or a halogen atom, and a group obtained by a Diels-Alder reaction of said group with a cyclodiene. Further, n is preferably an integer of from 1 to 4.

Specific but non-limitative examples of the unsaturated dicarboxylic anhydride which can be used in the above reaction system include maleic anhydride, citraconic anhydride, itaconic anhydride, tetrahydrophthalic anhydride, nadic anhydride, and products obtained by a Diels-Alder reaction of one of these anhydrides with a cyclodiene, and their halogen- or alkyl-substituted compounds. These compounds may be used either alone or in admixture.

In the foregoing formula for the amine or polyamine, specific examples of $R^1$ include the following groups:
(1) A straight or branched chain alkylene group having less than 13 carbon atoms.
(2) A cyclic alkylene group whose ring has 5 or 6 carbon atoms.
(3) A heterocyclic group containing at least one of oxygen, nitrogen, or sulfur atom.
(4) A phenylene or polycyclic aromatic group.
(5) Derivatives of the aforesaid groups enumerated in (1) to (4), which, however, do not adversely affect the reaction of this invention.
(6) Those in which a plurality of the phenylene or polycyclic aromatic groups described above in (4) are connected to each other either directly or via a divalent atom (such as oxygen or sulfur) or one of the groups enumerated below: —$NR^4$—, —P-(O)$R^5$—, —N=N—,

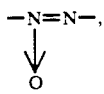

—CO—O—, —$SO_2$—, —$SiR^4R^5$—, —CONH—, —NY—CO—X—CO—NY—, —O—CO—X-—CO—O—,

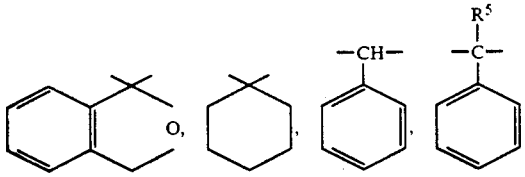

wherein $R^4$, $R^5$, and Y each represents an alkyl group having from 1 to 4 carbon atoms, a cyclic alkyl group whose ring has 5 or 6 carbon atoms, or a phenyl or polycyclic aromatic group; and X represents a straight chain alkylene group having less than 13 carbon atoms, a cyclic alkylene group having 6 carbon atoms, or a monocyclic or polycyclic arylene groups.

Specific but non-limitative examples of the amine or polyamine used in the present invention include methylamine, ethylamine, 1-propylamine, 1,2-dimethylpropylamine, 3-methoxypropylamine, 3-ethoxypropylamine, 3-propoxypropylamine, 3-isopropoxypropylamine, 3-butoxypropylamine, 3-isobutoxypropylamine, 3-(2-ethylhexyloxy)propylamine, 3-lauryloxypropylamine, 3-myristyloxypropylamine, methylaminopropylamine, dimethylaminopropylamine, diethylaminopropylamine, dibutylaminopropylamine, 2-hydroxyethylaminopropylamine, dimethylaminoethoxypropylamine, laurylaminopropylamine, diethanolaminopropylamine, iminobispropylamine, methylaminobispropylamine, n-butylamine, isobutylamine, sec-butylamine, hexylamine, 2-ethylhexylamine, dodecylamine, cyclohexylamine, allylamine, 3-decyloxyamine, dimethylaminoethylamine, diethylaminoethylamine, ethylaminoethylamine, α-phenethylamine, β-phenethylamine, furfurylamine, methoxylamine, m-aminobenzylamine, m-phenylenediamine, 4-chloro-m-phenylenediamine, 5-nitro-m-phenylenediamine, 4,6-dimethyl-m-phenylenediamine, p-phenylenediamine, 2-chloro-p-phenylenediamine, 2-nitro-p-phenylenediamine, 2-cyano p-phenylenediamine, 2,5-dichloro-p-phenylenediamine, 2,6-dichloro-p-phenylenediamine 2,5-diethyl-p-phenylenediamine, 2-chloro-5-methyl-p-phenylenediamine, tetrafluorophenylenediamine, tolylenediamine, 3,5-diethyl-2,4-toluylenediamine, 2-picolylamine, 3-picolylamine, 4-picolylamine, m-xylylenediamine, p-xylylenediamine, hexamethylene diamine, heptamethylenediamine, 4,4-dimethylheptamethylenediamine, diethylenetriamine, triethylenetetraamine, tetraethylenepentamine, pentaethylenehexamine, 4,4'-diaminodiphenylmethane, 3,4'-diaminodiphenylmethane, 3,3'-diaminodiphenylmethane, 3,3',4,4'-tetraminodiphenylmethane, 4,4'-diamino-3,3'-diethyldiphenylmethane, 4,4'-diamino-3,3'-diethyl-5,5'-dimethyldiphenylmethane, 4,4'-bis(p-aminophenoxy)diphenylmethane, 4,4'-bis(m-aminophenoxy)diphenylmethane, 2,2',3,3'-tetrachloro-4,4'-diaminodiphenylmethane, diaminodicyclohexylmethane, 4,4'-bis(p-aminophenoxy)diphenylethane, 4,4'-bis(m-aminophenoxy)diphenylethane, 1,2-bis(3-aminopropoxy)ethane, 2-aminopropanol, 3-aminopropanol, 1,2-diaminopropane, 1,3-diaminopropane, 4,4'-diaminodiphenylpropane, 3,3'-diaminodiphenylpropane, 1,2-bis(3-aminopropoxy)-2,2-dimethylpropane, 4,4'-bis(p-aminophenoxy)diphenylpropane, 4,4'-bis(m-aminophenoxy)diphenylpropane, 2,2-bis(4-aminophenyl)propane, 1,4-diaminobutane, 1,4-diaminocyclohexane, bis(3-aminopropyl) ether, α,ω-bis(3-aminopropyl)-polyethylene glycol ether, 3,3'-diaminodiphenyl ether, 3,4'-diaminodiphenyl ether, 4,4'-diaminodiphenyl ether, 3,4,4'-triaminodiphenyl ether, 3,3',4,4'-tetraaminodiphenyl ether, bis(p-β-amino-t-butylphenyl) ether, toluidine, 4,4'-methylenedi-o-toluidine, 4,4'-methylenedi-6-bromo-2-toluidine, aniline, ethylaniline, dichloroaniline, 4,4'-methylenedi-2,6-diethylaniline, 4,4'-methylenedi-2,6-isopropylaniline, isopropoxyaniline, chloroaniline, bromoaniline, iodoaniline, nitroaniline, 4,4'-methylenedi-2,6-dibromoaniline, 4,4'-methylenedi-2-bromo-6-chloroaniline, bis-p-aminophenylaniline, methylenebisanthranilic acid, methylenebismethylanthranilate, 3,3'-diaminodiphenyl sulfone, 4,4'-diaminodiphenyl sulfone, 3,3',4,4'-tetraaminodiphenyl sulfone, p-bis(4-aminophenoxy)diphenyl sulfone, p-bis(3-aminophenoxy)-diphenyl sulfone, 2,2-bis[4-(4-aminophenoxy)phenyl] sulfone, o-tolidine sulfone, 4,4'-diaminodiphenylsulfide, bis(4-aminophenyl) disulfide, 3,3',4,4'-tetraaminodiphenyl sulfide, N-aminoethylpiperidine, N-aminomethyl-4-pipecoline, N-aminoethylmorpholine, N-aminopropylpiperidine, N-aminopropyl-2-pipecoline, N-aminopropyl-4-pipecoline, N-aminopropylmorpholine, 2-aminoethylpiperidine, 4-aminomethylpiperidine, N-aminopyridine, 1-amino-4-methylpiperazine, 1,4-bisaminopropylpiperazine, N-aminopropylpiperazine, 1-amino-4-cyclophenylpiperazine, 2-aminopyrazine, 2-aminopyridine, 3-aminopyridine, 4-aminopyridine, 2,3-diaminopyridine, 2,5-diaminopyridine, 2,6-diaminopyridine, 2,3,6-triaminopyridine, 2-amino-3-methylpyridine, 2-amino-4-methylpyridine, 2-amino-5-methylpyridine, 2-amino-6-methylpyridine, 2-amino-4-ethylpyridine, 2-amino-4- propylpyridine, 2-amino-4,6-dimethylpyridine, 2,6-diamino-4-methylpyridine, 2-amino-3-nitropyridine, 2-amino-5-nitropyridine, 2-chloro-4-aminopyridine, 2-chloro-5-aminopyridine, 2-amino-3,5-dichloropyridine, 4-amino-3,5-dichloropyridine, 2-amino-3,5-dichloro-6-methylpyridine, 2-amino-3,5-dichloro-4-methylpyridine, 2-amino-5-chloro-3-methylpyridine, 2-amino-3,5-dichloro-4,6-dimethylpyridine, 2,4-diaminopyrimidine, 2,4-diamino-6-(4-pyridyl)-5-triazine, p-bis(4-aminophenoxy)benzene, m-bis(4-aminophenoxy)benzene, p-bis(3-aminophenoxy)benzene, m-bis(3-aminophenoxy)benzene, 1,3,5-triaminobenzene, 4,4'-diamino-3-methoxyazobenzene, 1,5-diaminonaphthalene, 1,3,5-triaminonaphthalene, 3,3'-dimethyl-4,4'-diaminobiphenyl, 4,4'-diaminooctafluorobiphenyl, 2,5-diaminoterephthalic acid, 3,4-diaminobenzanilide, 4,4'-diaminobenzanilide, 4-(p-aminophenoxy)-4-aminobenzanilide, 3,3'-dimethoxybenzidine, 3,3'-dimethylbenzidine, 3,3'-diaminobenzidine, 3,3'-dihydroxybenzidine, 2,2'-dichloro-5,5'-dimethoxybenzidine, 2,2',5,5'-tetrachlorobenzidine, 2,4-diaminotoluene, 2,4-bis(β-amino-t-butyl)toluene, 4,4'-diaminobenzophenone, polytetramethyleneoxide-di-p-aminobenzoate, trimethylenebis(4-aminobenzoate), bis(4-aminophenyl)diphenylsilane, bis(4-aminophenyl)dimethylsilane, bis(4-aminophenyl)phenylphosphineoxide, bis(4-aminophenyl)methylphosphineoxide, melamine, 4,4'-diaminostilbene, 9,9-bis(4-aminophenyl)-10-hydroanthracene 2,6-diaminoanthraquinone, 1,5-diaminoanthraquinone, 9,9-bis(4-aminophenyl)fluorene, 5-amino-1-(4'-aminophenyl)-1,3,3-trimethylindane, 6-amino-1-(4'-aminophenyl)-1,3,3-trimethylindane, anisidine, phenetidine, aminophenol, 2-aminothiophenol, 4-aminothiophenol, aminobenzoic acid, 2,5-diaminobenzoic acid, 3,5-diaminobenzoic acid, xylidine, 4,4'-methylenedi-2,6-xylidine, 2,6-diaminobenzothiazole, m-aminobenzoic acid hydrazide, 2,4-diaminomesitylene, hexaaminocyclophosphagen, 1,1-diamino-3,3,5,5-tetraphenoxycyclophosphagen, 1,3,5-tris(p-aminophenoxy)-1,3,5-triphenoxycyclophosphagen, and hexabis(p-aminophenoxy)cyclophosphagen. These compounds may be used either alone or in admixture.

Among of the above-enumerated amines and polyamines are particularly preferred diaminodiphenyl ethers, 4,4'-methylenedi-o-toluidine, m-phenylenediamine, 4,4'-diaminodiphenylmethane, aniline, 1,3,5-triaminobenzene, hexamethylenediamine, 3,3'-dimethyl-4,4'-diaminobiphenyl, toluylenediamine, 3,3'-diaminobenzidine, 3,3',4,4'-tetraaminodiphenylmethane, diaminodicyclohexylmethane, dichloroaniline, bromoaniline, 4,4'-diaminodiphenyl sulfone, and 4,4'-diaminodiphenyl sulfide.

In formula (III), $R^2$ and $R^3$, which may be the same or different, each represents a monovalent organic group having at least one carbon atom and preferably an alkyl group having from 1 to 4 carbon atoms. Specific but non-limitative examples of the orthoester include methyl orthoformate, ethyl orthoformate, propyl orthoformate, methyl orthoacetate, ethyl orthoacetate, propyl orthoacetate, methyl orthopropionate, ethyl orthopropionate, and propyl orthopropionate. These compounds may be used either alone or in admixture.

The conditions for the reaction between the orthoester and the unsaturated amide acid compound may vary depending on the types of the compounds. It is preferable to heat these materials to from 40° to 150° C., more preferably from 40° to 120° C., for from about 1 to 20 hours.

In the present invention, the ratio between the unsaturated amide acid compound and the orthoester is not particularly limited. It is preferable to employ from about 1.0 to 20.0 moles, more preferably from 1.0 to 10.0 moles, of the orthoester per mole of the carboxyl group contained in the unsaturated amide acid compound.

The above-mentioned reaction may be carried out either without using any solvent or in the presence of an inert organic solvent. Specific but non-limitative examples of the organic solvent include dimethylformamide, diethylformamide, dimethylacetamide, formamide, acetamide, N-methylpyrrolidone, 1,3-dimethyl-2-imidazolidinone, acetone, dioxane, benzene, toluene, xylene, hexane, cyclohexane, methyl ethyl ketone, methyl isobutyl ketone, diethyl ether, tetrahydrofuran, dimethyl carbitol, methanol, ethanol, propanol, phenol, and cresol. These solvents may be used alone or in admixture.

As the result of investigations made by the present inventors, it has been found that the reaction between the unsaturated amide acid compound and the orthoester proceeds as follows.

The above-described orthoester is, in general, useful as an esterifying agent and reacts with a carboxylic acid, whereby it is not only decomposed into (A) a low-molecular weight ester and (B) an alcohol but also esterifies the carboxylic acid with extremely good efficiency to give (C) a desired carboxylic acid ester, as illustrated in the following equation.

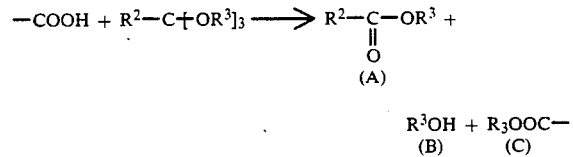

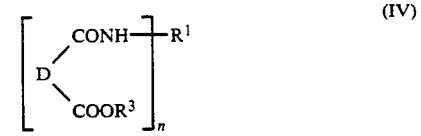

When the orthoester is mixed with the unsaturated amide acid compound, the carboxyl group(s) present in the unsaturated amide acid compound molecule react with the orthoester to form an unsaturated dicarboxylic acid amide acid ester of formula (IV):

$$\left[ D \diagup_{\diagdown COOR^3}^{\diagup CONH-R^1} \right]_n \quad (IV)$$

The inventors have confirmed that the orthoester esterifies the unsaturated amide acid compound by the $^{13}C$—NMR analysis.

Since the above-described low-molecular weight ester (A) and alcohol (B) are low-boiling point compounds, it is possible to successively remove them during the reaction. For example, they can be removed during the reaction only by installing a trap in the lower portion of a condenser. Further, it is also possible to remove them by distillation in vacuo or at atmospheric pressure after completion of the reaction. These steps are extremely simple as compared to the usual purification step, and a complicated purification step used in the conventional production step of an unsaturated amide acid compound is not needed.

The unsaturated dicarboxylic acid amide acid ester of formula (IV) thus formed is further heated. Then, the amide moiety is converted into an imide moiety through intramolecular dealcoholization, to give an unsaturated dicarboxylic acid imide compound of formula (I). Namely, during reaction carried out at from 40° to 150° C. for from 1 to 20 hours, the dealcoholization and esterification are achieved.

The dealcoholization readily occurs, as compared to they conventional dehydration reaction. According to the present invention, therefore, the cyclization requires less energy, i.e., a low temperature and short period of time, than the known methods do. Further, it is accompanied by no homopolymerization and, thus, the obtained product contains a small amount of polymer components. Furthermore, the unsaturated dicarboxylic acid amide acid ester which is the starting material in the dealcoholization can be formed very efficiently, as described above. Thus, the unsaturated dicarboxylic acid amide acid ester is highly pure, which brings about a high-purity final product, i.e., the unsaturated dicarboxylic acid imide compound.

When this reaction is carried out at a temperature lower than 40° C., the formation of the imide through the dealcoholization cannot be sufficiently conducted. As a result, the amide moiety remains in the molecule in this case. When the heating temperature exceeds 150° C., the formed unsaturated dicarboxylic acid imide compound is polymerized through self-polymerization. Therefore, it is preferable that the heating temperature falls within the range specified above.

Though the dealcoholization cyclization is accelerated under a reduced pressure of from about $10^{-3}$ to $10^{-5}$ mmHg, it can be conducted extremely efficiently under the reaction conditions specified in the present invention, even though a reduced pressure or other means is not employed. That is, if the reaction is carried out under a reduced pressure, it can be completed within a short period of time, even when it originally requires a long period of time. As a result, because of the short-period reaction, polymerization caused by, for example, reaction of the double bond(s) does not take place so that the product is highly pure. Further, this reaction brings about an advantage that apparatus for achieving the reduced pressure is not required.

In the above reaction, it is possible to subject the reaction mixture obtained from the unsaturated dicarboxylic anhydride and the amine or polyamine to the esterification and the subsequent dealcoholization as such without isolating the unsaturated amide acid compound. Needless to say, the unsaturated amide acid compound may be isolated from the reaction mixture and then used in the form of a powder.

It is also possible to react the unsaturated dicarboxylic acid imide acid ester of formula (IV) in a non-polar solvent in the presence of a basic catalyst to give the unsaturated dicarboxylic acid imide compound of formula (I).

Specific but non-limitative examples of the basic catalyst which can be used include tertiary amines such as triethylamine, trimethylamine, triethylenediamine, and tetramethylethylenediamine; and imidazoles such as imidazole, 2-methylimidazole, 2-ethyl-4-methylimidazole, 2-phenylimidazole, 1-benzyl-2-methylimidazole, 2-phenyl-4-methylimidazole, 1-cyanoethyl-2-methylimidazole, and 1-cyanoethyl-2-phenylimidazole.

In the present invention, the ratio between the basic catalyst and the unsaturated dicarboxylic acid amide acid ester of formula (IV) is not particularly limited. It is preferable to use from about 0.01 to 20 parts (by weight, the same will apply hereinafter), more preferably from 0.1 to 10 parts, of the basic catalyst based on 100 parts of the unsaturated dicarboxylic acid amide acid ester. When the amount of the basic catalyst is smaller than the above lower limit, the aimed effect is not often achieved. When it exceeds the above range, polymerization caused by, for example, reaction of the double bond(s) is liable to occur, resulting in a tendency of lowering the purity of the aimed unsaturated dicarboxylic acid imide compound. Although catalysts other than the basic catalyst, for example, an acid catalyst, may accelerate the above reaction, the effect of the former is much lower than that of the latter. The process of the present invention is further advantageous in that it requires neither any dehydrating agent nor any purification step, different from the known cyclization methods. In order to fully utilize this advantage, it is further preferable to select the low-boiling point catalyst which can be distilled off after the completion of the reaction from among those cited above.

Specific but non-limitative examples of the non-polar solvent to be used here include hexane, cyclohexane, benzene, toluene, xylene, carbon tetrachloride, 1,2-dichloroethylene, diethyl ether, diisopropyl ether, tetrahydrofuran, 1,4-dioxane, and diethylene glycol dimethyl ether.

In the present invention, the ratio between the non-polar solvent and the unsaturated dicarboxylic acid amide acid ester of formula (IV) is not particularly limited. It is preferable to use from about, 100 to 2000 parts, more preferably from 100 to 900 parts, of the non-polar solvent based on 100 parts of the unsaturated dicarboxylic acid amide acid ester.

When a polar solvent is used, some side reactions other than the aimed cyclization, for example, a reaction between double bonds, are liable to occur, resulting in a tendency of lowering the purity of the aimed unsaturated dicarboxylic acid imide compound.

The conditions for the reaction of the unsaturated dicarboxylic acid amide acid ester of formula (IV) in a non-polar solvent in the presence of a basic catalyst vary depending on the type and amount of the catalyst as well as those of the solvent. It is preferable to carry out this reaction at from 40° to 150° C., more preferably from 60° to 100° C., for from about 1 to 10 hours, more preferably from 1 to 3 hours.

When the reaction temperature is lower than the above range and/or the reaction period is shorter than the above range, the reaction does not often fully proceed. When the reaction temperature and/or the reaction period exceeds the above range, some side reactions such as polymerization through a reaction between double bonds are liable to occur, resulting in a tendency of lowering the purity of the aimed unsaturated dicarboxylic acid imide compound.

As described above, in the process of the present invention for producing the unsaturated dicarboxylic acid imide compound, the reaction between the starting unsaturated amide acid compound and the orthoester is highly efficient esterification. Further, the cyclization of the unsaturated dicarboxylic acid amide ester thus obtained is a dealcoholization which does not requires such a high energy as the conventional dehydration does. Thus, the overall reaction can be efficiently conducted with the use of a low energy. Consequently, the unsaturated dicarboxylic acid imide compound thus obtained contains only a small amount of polymer components and has high purity.

Thus, the unsaturated dicarboxylic acid imide compound obtained by the present invention is highly useful as a laminated board for printed circuit board or as a molding material which should have high thermal resistance as well as high purity. When the unsaturated dicarboxylic acid imide compound is formulated into a laminated board or a molding material, other components may be added thereto in an appropriate ratio, if required.

The unsaturated dicarboxylic acid imide compound obtained by the process of the present invention may be conveniently formulated into, for example, the above-mentioned laminated board by using a prepreg impregnated with the unsaturated dicarboxylic acid imide compound. This prepreg may be obtained by, for example, the following method. Namely, the unsaturated dicarboxylic acid imide compound is dissolved in a solvent, and other components are added thereto in an appropriate ratio, if desired, to give a varnish. Then, a substrate is impregnated with this varnish and evaporated to dryness. Alternatively, the above-described compound is further semi-solidified to give a prepreg. The solution which is obtained during the synthesis of the unsaturated dicarboxylic acid imide compound may be employed as the above-mentioned varnish either as such or as a mixture with additional appropriate components. The substrate to be used here is not particularly limited. For example, inorganic cloths such as glass cloth or quartz fiber cloth, or high heat-resistance fiber cloths such as aromatic polyamide fiber (Aramid fiber) may be used therefor. In general, this substrate is surface-treated with, for example, a coupling agent and then provided for use. The semi-solidification may be preferably carried out at from 120° to 250° C. A temperature exceeding the above range might make molding difficult. On the other hand, the solidification might not fully proceed at an excessively low temperature.

The above-mentioned laminated board may be prepared in the following manner. The desired number of the above-mentioned prepregs are laminated, and metal foils and printed boards are further laminated thereon, if required. After molding, the aimed laminated board is obtained. Since the resulting laminated board comprises the unsaturated dicarboxylic acid imide compound obtained by the present invention, it has high heat resistance, high adhesiveness and excellent insulating properties. Examples of the above mentioned metal foil include copper and nickel foils.

To further illustrate the present invention, the following Examples and Comparative Examples are given.

EXAMPLE 1

49.0 g (0.5 mole) of maleic anhydride which is an unsaturated dicarboxylic anhydride was dissolved in 150 g of acetone. Separately, 49.5 g (0.25 mole) of 4,4'-diaminodiphenylmethane which is a polyamine was dissolved in 150 g of acetone. The obtained maleic anhydride solution was stirred at 20° C., and the 4,4'-diaminodiphenylmethane solution was added dropwise thereto within approximately one hour. Then, the resulting mixture was stirred for two hours while keeping at 20° C., to complete the reaction. To the obtained reaction mixture was added 250 g of water. The precipitate thus formed was filtered, washed with water, and dried to give 93.8 g of a product. The structure of this product was analyzed by $^{13}C$—NMR. As a result, it was identified as an unsaturated amide acid (N,N'-4,4'-diphenylmethanebismaleamic acid) of the following structure:

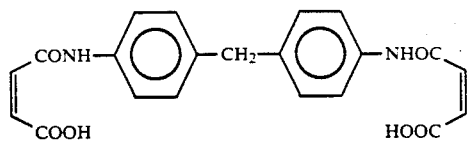

The purity of this compound determined by liquid chromatography was 98.5%.

8.5 g (0.25 mole) of the N,N'-4,4'-diphenylmethanebismaleamic acid thus obtained was dissolved in 100 g of dimethylacetamide. To the obtained solution was added 60.0 g (0.5 mole) of methyl orthoacetate which is an orthoester, having the following structure, and the mixture was allowed to react at 80° C. for one hour.

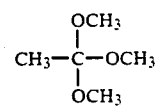

After one hour, the temperature was lowered to 20° C. to complete the reaction. To the resulting reaction mixture was added 250 g of water. The precipitate thus formed was filtered, washed with water, and then dried. Thus, 100 g of a yellow reaction product was obtained. The structure of this product was analyzed by $^{13}C$—NMR. As a result, it was identified as an unsaturated dicarboxylic acid amide acid ester (dimethyl bismaleamate) of the following structure:

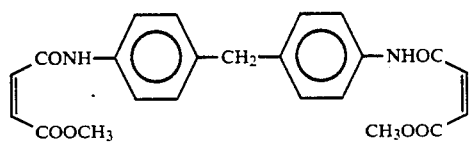

The purity of this product determined by high performance liquid chromatography was 98.0%.

100 g of the methylbismaleamate thus obtained was dissolved in 100 g of dimethylacetamide, and the resulting solution was allowed to react at $10^{-3}$ mmHg and 40° C. for two hours. After completion of the reaction, 250 g of water formed was filtered, washed with water, and dried to give 83.2 g of a reaction product. The structure of this product was analyzed by $^{13}C$—NMR. As a result, it was identified as an unsaturated dicarboxylic acid imide compound (maleic acid N,N'-4,4'-diphenylmethane-bisimide) of the following structure:

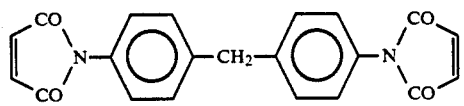

The purity of this product determined by liquid chromatography was 97.5%.

In this Example, the esterified product was once taken out from the solution and then converted into a solution again prior to the dealcoholization. This step was carried out in order to confirm the product and yield of the esterification. Namely, the process of the present invention does not essentially involve this step. The thus obtained unsaturated dicarboxylic acid amide acid ester is as identified by $^{13}$C—NMR. As shown in FIG. 1, the formation of the aimed unsaturated dicarboxylic acid amide acid methyl ester was confirmed. As described above, the dealcoholization was carried out at an extremely low energy, and the esterified product was unstable. Therefore, it is not preferable to store the esterified product for a long period of time as such. Thus, it is preferable in practice to continuously effect the esterification and the dealcoholization in the same reaction system. However, it is possible to take out the esterified product from the reaction system for a short period of time so that spontaneous dealcoholization does not take place.

EXAMPLE 2

49.0 g (0.5 mole) of maleic anhydride was dissolved in 50 g of dimethylacetamide. Separately, 49.5 g (0.25 mole) of 4,4'-diaminodiphenylmethane was dissolved in 50 g of dimethylacetamide. These solutions thus obtained were reacted under the same conditions as in Example 1. To the obtained reaction mixture was added 81.0 g (0.5 mole) of ethyl orthoacetate, and the resulting mixture was allowed to react for one hour while keeping at 80° C. Then, the reaction mixture was allowed to react as such at $10^{-3}$ mmHg and 40° C. for an additional two hours to complete the reaction. To the obtained reaction mixture was added 250 g of water, filtered, and then dried to give 85.5 g (yield: 95.0%) of an unsaturated dicarboxylic acid imide compound (maleic acid N,N'-diphenylmethanebisimide). The purity of this product determined by liquid chromatography was 97.8%.

EXAMPLE 3

The procedure of Example 2 was repeated, except that 53.0 g (0.5 mole) of methyl orthoformate was used as the orthoester. Thus, 84.1 g (yield: 94.6%) of an unsaturated dicarboxylic acid imide compound was obtained. The purity of this product determined by liquid chromatography was 97.5%.

EXAMPLE 4

To 98.5 g (0.25 mole) of the N,N'-4,4'-diphenylmethanebismaleamic acid obtained in Example 1 was added 810 g (5.0 moles) of ethyl orthoacetate. The resulting mixture was allowed to react at 80° C. for one hour under stirring without using any solvent. Subsequently, the reaction mixture was allowed to react at a temperature of 40° C. and $10^{-3}$ mmHg for two hours. Thus, 83.0 g (yield: 92.7%) of an unsaturated dicarboxylic acid imide compound was obtained. The purity of this product determined by liquid chromatography was 95.0%.

EXAMPLE 5

The procedure of Example 2 was repeated, except that 100 g of dimethylformamide was used as the solvent. Thus, 85.3 g (yield: 95.3%) of an unsaturated dicarboxylic acid imide compound was obtained. The purity of this product determined by liquid chromatography was 97.5%.

EXAMPLE 6

49.0 g (0.5 mole) of maleic anhydride was dissolved in 50 g of dimethylformamide. Separately, 46.5 g (0.5 mole) of aniline which is an amine was dissolved in 50 g of dimethylformamide. The resulting solutions were reacted under the same conditions as in Example 1. To the resulting reaction mixture was added 60.0 g (0.5 mole) of methyl orthoacetate, and the reaction mixture was allowed to react for one hour while keeping at a temperature of 80° C. Then, it was further reacted at 100° C. for an additional two hours to complete the reaction. To the obtained reaction mixture was added 250 g of water. The precipitate thus formed was filtered, washed with water, and then dried to give 82.0 g of a reaction product. The structure of this product was analyzed by $^{13}$C—NMR. As a result, it was identified as an unsaturated dicarboxylic acid imide compound of the following structure:

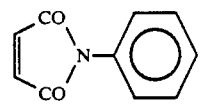

The purity of this compound determined by liquid chromatography was 97.5%.

EXAMPLE 7

The procedure of Example 6 was repeated, except that 150.0 g (0.51 mole) of maleic anhydride and 20.9 g (0.17 mole) of 1,3,5-triaminobenzene as a polyamine were used and dissolved in 20 g of dimethylacetamide. The structure of this product was analyzed by $^{13}$C—NMR. As a result, it was identified as an unsaturated dicarboxylic acid imide compound of the following structure:

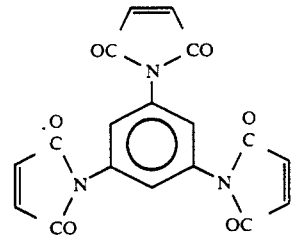

The purity of this compound determined by liquid chromatography was 95.4%.

COMPARATIVE EXAMPLE 1

21.6 g of maleic anhydride was dissolved in 210 ml of 1,2-dichloromethane. Separately, 19.8 g of 4,4'-diaminodiphenylmethane was dissolved in 24 ml of dimethylformamide. The maleic anhydride solution thus obtained was stirred at 25° C., and the 4,4-diaminodiphenylmethane solution was slowly added dropwise thereto. The resulting mixture was stirred at 25° C. for an additional three hours. Then, 2.9 g of p-toluenesulfonic acid was added thereto, and the temperature was elevated to 84° C. The obtained mixture was subjected to heat cyclization for 20 hours, while removing the water thus formed by azeotropic distillation. After completion of the reaction, the 1,2-dichloromethane was evaporated off from the reaction mixture to give a concentrate to which 100 g of water was then added. The precipitate thus formed was filtered, washed successively with water, an aqueous solution of sodium carbonate and water, and then dried.

Thus, 34 g of an unsaturated dicarboxylic acid imide compound (maleic acid N,N'-4,4'-diphenylmethanebisimide) was obtained. The purity of this compound determined by liquid chromatography was low as 92.2%.

COMPARATIVE EXAMPLE 2

To 98.5 g (0.25 mole) of the N,N'-4,4'-diphenylmethanebismaleamic acid obtained in Example 1 was added 250 ml of acetone, followed by stirring and mixing. To this solution were added 0.63 g of cobalt naphthenate, 10.0 g of triethylamine, and 71.4 g of acetic anhydride. The resulting mixture was subjected to chemical cyclization at 55° C. for two hours. After completion of the reaction, the temperature was lowered to 20° C., and 250 g of water was added to the mixture. The precipitate thus formed was filtered, washed successively with water, an aqueous solution of sodium carbonate and water, and then dried. Thus, 81.5 g of an unsaturated dicarboxylic acid imide compound (maleic acid N,N'-4,4'-diphenylmethanebisimide) was obtained. The purity of this compound determined by liquid chromatography was low as 90.1%.

EXAMPLE 8

211 g (0.5 mole) of the methyl N,N'-4,4'-diphenylmethanebismaleamidate was dissolved in 50 g of 1,4-dioxane, and 21.1 g of triethylamine was added thereto. The obtained mixture was allowed to react at 100° C. for three hours. After completion of the reaction, 500 g of water was added to the reaction mixture. The precipitate thus formed was filtered, washed with water, and then dried. Thus, 175 g of a reaction product was obtained. The structure of the reaction product was analyzed by $^{13}C$—NMR. As a result, it was identified as an unsaturated dicarboxylic acid imide compound (N,N'-4,4'-diphenylmethanebismaleimide) of the following structure:

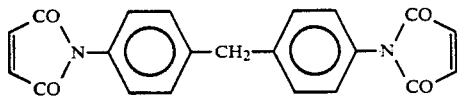

The purity of this product determined by liquid chromatography was 97.5%.

EXAMPLE 9

The reaction of Example 8 was repeated. After completion of the reaction, the reaction mixture was distilled under a reduced pressure of $10^{-3}$ mmHg at 40° C. to remove the solvent and catalyst. Thus, 179 g of an unsaturated dicarboxylic acid imide compound (N,N'-4,4'-diphenylmethanebismaleimide) was obtained. The purity of this product determined by liquid chromatography was 96.0%.

EXAMPLE 10

176 g of an unsaturated dicarboxylic acid imide compound obtained in the same manner as in Example 9 was dissolved in 163 g of N,N-dimethylacetamide without being isolated. To the obtained solution was added 66 g of diaminodiphenylmethane, and the mixture was allowed to react at 80° C. for three hours. A glass cloth was impregnated with the varnish thus obtained and then dried at 150° C. for five minutes, to give a prepreg containing 50%, based on the total weight, of the resin. Four these prepregs were laminated together, and copper foils were further laminated onto both sides of the laminate. The obtained material was molded at 140° C. for 60 minutes under 40 kg-f/cm² and then cured at 230° C. for two hours. Thus, a double sided copper foil-laminated board was obtained.

The Tg of this laminated board determined by the TMA analysis was 250° C. The adhesion strength among the prepregs was 1.3 kg-f/cm².

EXAMPLE 11

205 g (mole) of an unsaturated dicarboxylic acid amide acid ester of the following structure:

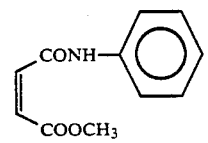

(methyl N-phenylmaleamidate) obtained in the same manner as in Example 1 was dissolved in 478 g of toluene, and 2.05 g of 1-benzyl-2-methylimidazole was added thereto. The obtained mixture was allowed to react at 80° C. for two hours. After completion of the reaction, 500 g of water was added to the reaction mixture. The precipitate thus formed was filtered, washed with water, and then dried to give 168 g of a reaction product. The analysis regarding the structure of this product by $^{13}C$—NMR indicated that it was an unsaturated dicarboxylic acid imide compound (N-phenylmaleimide) of the following structure:

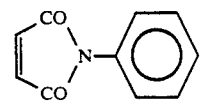

The purity of this unsaturated dicarboxylic acid imide compound determined by liquid chromatography was 97.5%.

The process for producing an unsaturated dicarboxylic acid imide compound of the present invention has been described above. That is, the starting reaction between the unsaturated amide acid compound and the orthoester is highly efficient esterification, and the subsequent cyclization of the obtained unsaturated dicarboxylic acid amide acid ester is dealcoholization which does not require such a high energy as the conventional dehydration does. Therefore, the whole reaction can be efficiently conducted with the use of a low energy. Consequently, the unsaturated dicarboxylic acid imide compound thus obtained contains a small amount of polymer component and has a high purity.

While the invention has been described in detail and with reference to specific embodiments thereof, it will be apparent to one skilled in the art that carious changes and modifications can be made therein without departing from the spirit and scope thereof.

What is claimed is:

1. A process for producing an unsaturated dicarboxylic acid imide compound of formula (I):

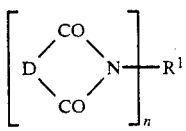 (I)

wherein D represents a group of the following formula:

where Z represents hydrogen, an alkyl group, a halogen atom or a group obtained by a Diels-Alder reaction of said group with a cyclodiene;

$R^1$ represents
(1) a straight or branched chain alkylene group having less than 13 carbon atoms;
(2) a cyclic alkylene group whose ring has 5 or 6 carbon atoms;
(3) a heterocyclic group containing at least one of an oxygen, nitrogen, or sulfur atom;
(4) a phenylene or polyacyclic aromatic group;
(5) derivatives of the aforesaid groups enumerated in (1) to (4), which do not adversely affect the reaction;
(6) groups in which a plurality of the phenylene or polycyclic aromatic groups described above in (4) are connected to each other either directly or via a divalent atom or one of the groups enumerated below: $-NR^4$, $-P(O)R^5-$, $-N=N-$,

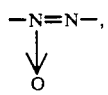

$-CO-O-$, $-SO_2$, $-SiR^4R^5-$, $-CONH-$, $-NY-CO-X-CO-NY-$, $-O-CO-X-CO-O-$,

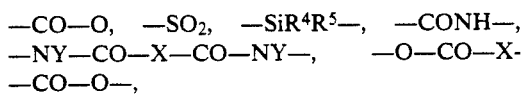

wherein $R^4$, $R^5$, and Y each represents an alkyl group having from 1 to 4 carbon atoms, a cyclic alkyl group whose ring has 5 or 6 carbon atoms, or a phenyl or polycyclic aromatic group; and X represents a straight chain alkylene group having less than 13 carbon atoms, a cyclic alkylene group having 6 carbon atoms, or a monocyclic or polycyclic arylene group; and n is an integer of 1 to 4, which comprises reacting an unsaturated amide acid compound of formula (II):

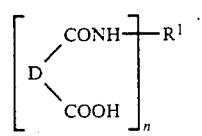 (II)

wherein D, $R^1$, and n are as defined above, with an orthoester of formula (III):

$$R^2-C(-OR^3)_3 \quad (III)$$

wherein $R^2$ and $R^3$, which may be the same or different, each represents an alkyl group having from 1 to 4 carbon atoms to form an unsaturated dicarboxylic acid amide acid ester compound of formula (IV):

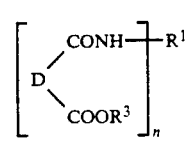 (IV)

wherein D, $R^1$, $R^3$, and n are as defined above, and then imidating the compound of formula (IV), wherein said unsaturated dicarboxylic acid amide acid ester compound of formula (IV) is imidated in a non-polar solvent, and in the presence of a basic catalyst, wherein said non-polar solvent is used in an amount of from about 100 to 2000 parts by weight based on 100 parts by weight of said unsaturated dicarboxylic acid amide acid ester compound of formula (IV) and wherein said basic catalyst is used in an amount of from about 0.01 to 20 parts by weight based on 100 parts by weight of said unsaturated dicarboxylic acid amide ester compound of formula (IV).

2. A process as in claim 1, wherein said orthoester of formula (III) is used in an amount of from about 1.0 to 20.0 moles per mole of the carboxyl group contained in said unsaturated amide acid compound of formula (II).

3. A process as in claim 1, wherein said unsaturated amide acid compound of formula (II) is reacted with said orthoester of formula (III) at from 40° to 150° C. for from about 1 to 20 hours.

4. A process as in claim 1, wherein said basic catalyst is a low-boiling point catalyst which can be distilled off after completion of the reaction.

5. A process as in claim 1, wherein said non-polar solvent is used in an amount of from about 100 to 2000 parts by weight based on 100 parts by weight of said unsaturated dicarboxylic acid amide acid ester compound of formula (IV).

6. A process as in claim 1, wherein said unsaturated dicarboxylic acid amide acid ester compound of formula (IV) is imidated at from 40° to 150° C. for from about 1 to 10 hours.

7. A process as in claim 1, wherein said unsaturated dicarboxylic acid amide acid ester compound of formula (IV) is esterified at from 40° to 150° C. for from about 1 to 10 hours.

8. A process as in claim 1, wherein the overall reaction for producing the unsaturated dicarboxylic acid imide compound of formula (I) from the unsaturated amide acid compound of formula (II) is carried out at from 40° to 150° C. for from about 1 to 20 hours.

9. A process as in claim 1, wherein said orthoester of formula (III) is at least one member selected from the group consisting of methyl orthoformate, ethyl orthoformate, propyl orthoformate, methyl orthoacetate, ethyl orthoacetate, propyl orthoacetate, methyl orthopropionate, ethyl orthopropionate, and propyl orthopropionate.

10. A process as in claim 1, wherein the esterification is carried out without using any solvent.

11. A process as in claim 1, wherein said non-polar solvent is at least one member selected from the group consisting of hexane, cyclohexane, benzene, toluene, xylene, carbon tetra chloride, 1,2-dichloroethylene, diethyl ether, diisopropyl ether, tetrahydrofuran, 1,4-dioxane, and diethylene glycol dimethyl ether.

12. A process as in claim 1, wherein said basic catalyst is at least one member selected from the group consisting of triethylamine, trimethylamine, triethylenediamine, tetramethylethylene diamine, imidazoles such as imidazole, 2-methylimidazole, 2-ethyl-4-methylimidazole, 2-phenylimidazole, 1-benzyl-2-methylimidazole, 2-phenyl-4-methylimidazole, 1-cyanoethyl-2-methylimidazole, and 1-cyanoethyl-2-phenylimidazole.

* * * * *

UNITED STATES PATENT AND TRADEMARK OFFICE
CERTIFICATE OF CORRECTION

PATENT NO. : 5,112,989

DATED : May 12, 1992

INVENTOR(S) : Tatsuo Yonemoto, Eiichiro Saito, Masahiro Matsumura

It is certified that error appears in the above-identified patent and that said Letters Patent is hereby corrected as shown below:

In claim 1, at column 15, about lines 12-16 of claim 1, delete $$\begin{array}{c} Z \\ | \\ -C- \\ | \\ -C- \\ | \\ Z \end{array}$$

and insert therefor $$--\begin{array}{c} Z \\ | \\ -C- \\ \| \\ -C- \\ | \\ Z \end{array}--$$

Signed and Sealed this

Twenty-ninth Day of November, 1994

Attest:

BRUCE LEHMAN

Attesting Officer     Commissioner of Patents and Trademarks